United States Patent
Willems et al.

[11] Patent Number: 6,002,955
[45] Date of Patent: Dec. 14, 1999

[54] STABILIZED ELECTROPHYSIOLOGY CATHETER AND METHOD FOR USE

[75] Inventors: Stephan Willems; Christian Weiss, both of Hamburg, Germany; Frank Nguyen, San Jose, Calif.; John W. Gaiser, Mountain View, Calif.; Scott A. McIntosh, Pacifica, Calif.

[73] Assignee: Medtronic, Inc., Minneapolis, Minn.

[21] Appl. No.: 08/949,408

[22] Filed: Oct. 14, 1997

Related U.S. Application Data

[63] Continuation-in-part of application No. 08/865,331, May 29, 1997, abandoned
[60] Provisional application No. 60/030,729, Nov. 8, 1996.

[51] Int. Cl.$^6$ .............................. A61N 1/05; A61B 5/04
[52] U.S. Cl. ............................................ 600/374; 607/125
[58] Field of Search .................................... 607/122, 125; 600/373–375, 381; 606/41

[56] References Cited

U.S. PATENT DOCUMENTS

| | | |
|---|---|---|
| 4,784,639 | 11/1988 | Patel . |
| 4,909,787 | 3/1990 | Danforth . |
| 4,960,134 | 10/1990 | Webster, Jr. . |
| 5,058,595 | 10/1991 | Kern . |
| 5,215,540 | 6/1993 | Anderhub . |
| 5,290,229 | 3/1994 | Paskar . |
| 5,304,131 | 4/1994 | Paskar . |
| 5,383,923 | 1/1995 | Webster, Jr. . |
| 5,405,375 | 4/1995 | Ayers et al. . |
| 5,423,772 | 6/1995 | Lurie et al. . |
| 5,431,168 | 7/1995 | Webster, Jr. . |
| 5,445,148 | 8/1995 | Jaraczewski et al. . |
| 5,465,717 | 11/1995 | Imran et al. . |
| 5,482,037 | 1/1996 | Borghi . |
| 5,487,385 | 1/1996 | Avitall . |
| 5,492,119 | 2/1996 | Abrams . |
| 5,509,411 | 4/1996 | Littmann et al. . |
| 5,524,619 | 6/1996 | Ouchi et al. . |
| 5,526,810 | 6/1996 | Wang . |
| 5,545,200 | 8/1996 | West et al. . |
| 5,549,581 | 8/1996 | Lurie et al. . |
| 5,626,136 | 5/1997 | Webster, Jr. et al. ................... 600/374 |
| 5,632,734 | 5/1997 | Galel et al. ............................. 604/282 |
| 5,640,955 | 6/1997 | Ockuly et al. .......................... 600/374 |
| 5,823,955 | 10/1998 | Kuck et al. ............................. 600/374 |
| 5,876,340 | 3/1999 | Tu et al. ................................ 600/439 |

FOREIGN PATENT DOCUMENTS 0 616 794 A1  9/1994  European Pat. Off. .

OTHER PUBLICATIONS

B Avitall et al., *PACE*, vol. 17, Part I, May 1994, pp. 908–918.
W M Jackman, MD, "Catheter Ablation of Right Atriofascicular (Mahaim) Accessory PAthways", Univ of Oklahoma Health Sciences Center, Oklahoma City, OK, Apr. 10, 1995.
Webster Laboratories, "Webster Laboratories Halo Catheter–Deflectable Tip", Product Reference Information, at least by Aug. 20, 1996.
Electro–Catheter Corporation, "Angled Genesis Steerable Catheter", Product Information, at least by Aug. 23, 1995.

*Primary Examiner*—Jeffrey R. Jastrzab
*Attorney, Agent, or Firm*—Daniel W. Latham; Harold R. Patton

[57] ABSTRACT

A stabilized electrophysiology catheter (4) includes a main body portion (16) and a flexible tip portion (18). A plurality of electrodes (24, 26) are positioned along the tip portion. The tip portion includes a main section (20) and a precurved, offset, reverse-angle anchor section (22) at its distal end. The anchor section is shaped to engage with and anchor to a coronary opening, typically the coronary sinus opening (48) in the right atrium or a pulmonary vein opening (82) in the left atrium, for stabilized mapping and ablation of the right atrium or the left atrium. A manipulator wire (36) is used to radially deflect the tip portion in a first direction (40). When introduced through the superior vena cava (46), the tip portion forms a generally J-shape. When introduced through the inferior vena cava (54), the tip portion is deflected more than 360°.

40 Claims, 13 Drawing Sheets

STABILIZED ELECTROPHYSIOLOGY CATHETER AND METHOD FOR USE

CROSS-REFERENCE TO RELATED APPLICATIONS

This application claims the benefit of, and is a Continuation-in-Part of, Provisional Patent Application No. 60/030,729 filed Nov. 8, 1996. This application is also a Continuation-in-Part of U.S. patent application Ser. No. 08/865,331 filed May 29, 1997 now abandoned.

BACKGROUND OF THE INVENTION

The present invention relates generally to steerable catheters, and more specifically to steerable electrophysiology catheters for use in mapping and ablation of cardiac tissue.

The heart includes a number of pathways which are responsible for the propagation of signals necessary for normal electrical and mechanical function. The present invention is concerned with treatment of tachycardia, abnormally rapid rhythms of the heart caused by the presence of an arrhythmogenic site or accessory pathway which bypasses or short circuits the normal pathways in the heart. Tachycardias may be defined as ventricular tachycardias (VTs) and supraventricular tachycardias (SVTs). VTs originate in the left or right ventricle and are typically caused by arrhythmogenic sites associated with or without underlying heart disease. SVTs originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, drugs typically only ask the symptoms and do not cure the underlying cause. Implantable devices, on the other hand, usually can correct an arrhythmia only after it occurs. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radiofrequency electrical energy, laser energy, and the like.

Of particular interest to the present invention, are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the accessory pathway. By successfully destroying that tissue, the abnormal signaling patterns responsible for the tachycardia cannot be sustained. Methods and systems for performing RF ablation by controlling temperature at the ablation site are described in U.S. Pat. No. 5,540,681 entitled "Method and System for Radiofrequency Ablation of Tissue."

Catheters designed for mapping and ablation frequently include a number of individual electrode bands mounted to the distal tip of the catheter so as to facilitate mapping of a wider area in less time, or to improve access to target sites for ablation. Such catheters are described in U.S. Pat. No. 5,445,148 entitled "Intracardiac Electrical Potential Reference Catheter." As described in that patent, it is frequently desirable to deflect the distal tip of the catheter into a non-linear configuration such as a semicircle, which facilitates access to substantially all of the heart walls to be mapped or ablated. Such deflection may be accomplished through the use of pull wires secured to the distal tip which can be tensioned from the proximal end of the catheter to deflect the tip in the desired configuration. In addition, mapping and ablation catheters may facilitate rotational positioning of the distal tip, either by rotating the entire catheter from the proximal end, or by exerting torque on a core wire secured to the distal tip without rotating the catheter body itself. See U.S. Pat. No. 5,545,200 entitled "Steerable Electrophysiology Catheter."

Catheters utilized in radiofrequency ablation are inserted into a major vein or artery, usually in the neck or groin area, and guided into the chambers of the heart by appropriate manipulation through the vein or artery. Such catheters must facilitate manipulation of the distal tip so that the distal electrode can be positioned against the tissue region to be ablated. The catheter must have a great deal of flexibility to follow the pathway of the major blood vessels into the heart, and the catheter must permit user manipulation of the tip even when the catheter is in a curved and twisted configuration. Because of the high degree of precision required for proper positioning of the tip electrode, the catheter must allow manipulation with a high degree of sensitivity and controllability. In addition, the distal portion of the catheter must be sufficiently resilient in order to be positioned against the wall of the heart and maintained in a position during ablation without being displaced by the movement of the beating heart.

SUMMARY OF THE INVENTION

The present invention is directed to a stabilized electrophysiology catheter finding a special utility for mapping and ablating cardiac tissue within the right atrium, especially in the vicinity of the opening to the coronary sinus.

The stabilized electrophysiology catheter includes a catheter shaft having a main body portion and a flexible tip portion. A plurality of electrodes are positioned along the tip portion. The tip portion includes a main section and an anchor section at the distal end of the tip portion. A radial deflector element extends along the catheter shaft and is coupled to the tip portion so the tip portion can be radially deflected in a first direction by longitudinal movement of the first manipulator element. In one embodiment the tip portion can be deflected beyond 360° to create an overlapping loop, if desired.

The anchor section is configured to engage with and anchor to a cardiac structure, such as the ostium or opening of a vessel. The anchor section is offset from the main section and is preferably a reverse angle anchor section so that it extends in a direction opposite the direction of curvature of the main section. The anchor section could be a curved section but preferably extends at an obtuse angle, such as 140°, to the main section. The anchor section is also preferably pre-formed to its offset configuration; however, the anchor section could be actively manipulatable into its offset configuration.

The invention finds particular utility in mapping, pacing and ablation of the right atrium with the anchor section engaged with the opening to the coronary sinus. Introduced through the superior vena cava, the tip portion can form a generally J-shape as it is biased against the chamber wall and, typically, extends along the tricuspid annulus. Similarly, the J-shaped portion of the tip can be positioned across the tricuspid valve or across the mitral valve for stability. When introduced into the right atrium through the inferior vena cava, the tip portion can be deflected more than 360° as it engages the chamber wall.

The invention can also be used in the left atrium with the anchor section anchored at the opening of any of the pulmonary veins. The tip portion may be deflectable, such as through the use of a core wire, to torque or laterally deflect all or part of the tip portion, preferably the proximal tip portion. With the anchor section engaging an opening in the heart, the entire catheter shaft can be rotated or torqued by rotating or torquing the catheter handle to laterally deflect the curved tip portion in an effective manner.

Other features and advantages of the invention will appear from the following description in which the preferred embodiments have been set forth in detail in conjunction with the accompanying drawings.

DESCRIPTION OF THE PREFERRED EMBODIMENT

Figures 1, 1A, 2A, 2B, 2C:
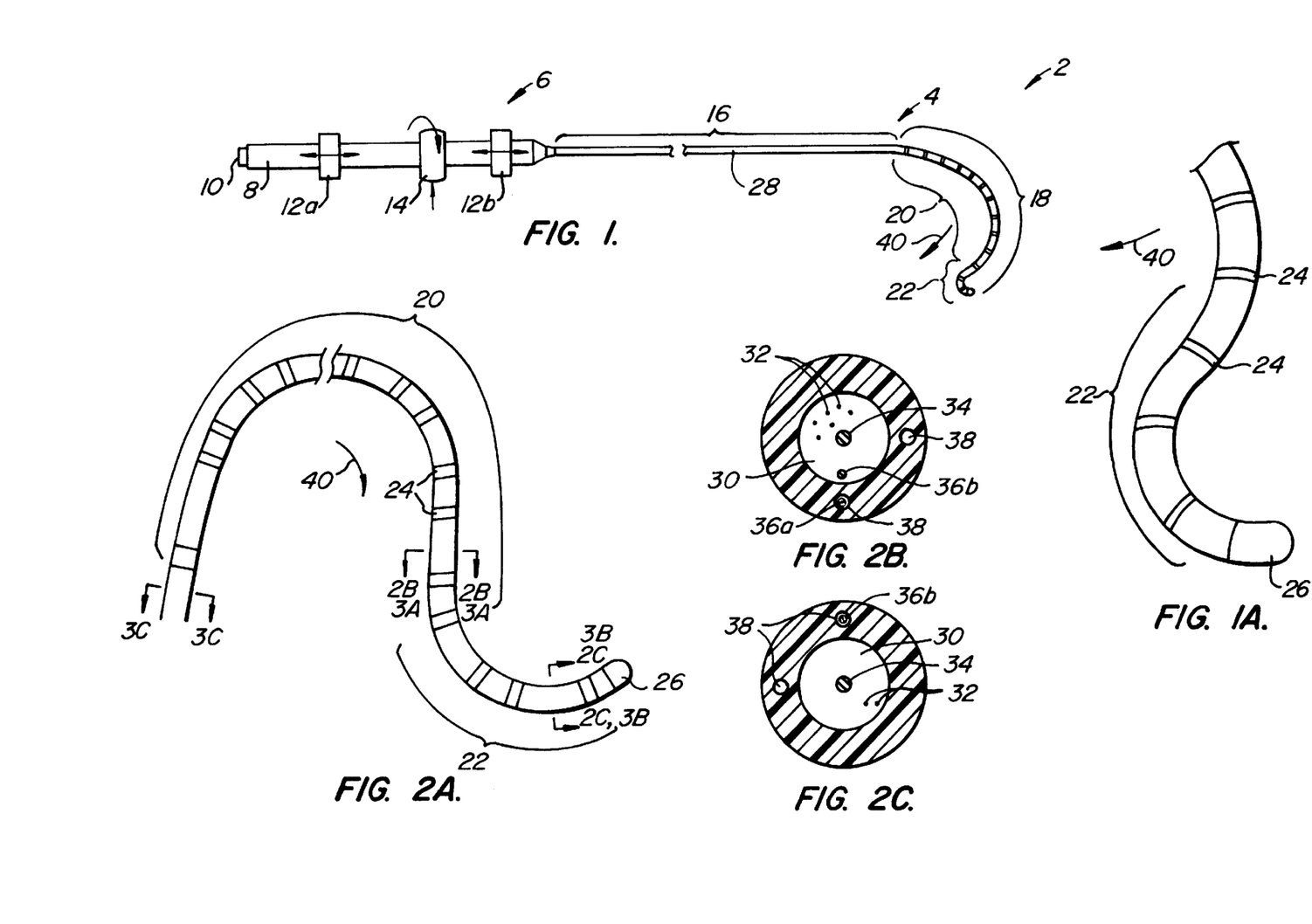
FIG. 1 illustrates, in simplified form, a catheter assembly made according to the invention.
FIG. 1A is an enlarged view of an end section of the tip portion of FIG. 1.
FIG. 2A is an enlarged view of the tip portion of FIG. 1.
FIGS. 2B and 2C are cross-sectional views taken along line 2B—2B and 2C—2C of FIG. 2A.

FIG. 1 illustrates an electrophysiology catheter assembly 2 made according to the invention. Catheter assembly 2 includes broadly a catheter 4 extending from a proximal assembly 6. Proximal assembly 6 includes a handle 8 to which an electrical connector 10 is mounted. Longitudinally slidable manipulator wire control elements 12a and 12b and a rotatable core wire control element 14 are movably mounted to handle 8 and are used to manipulate catheter 4 as discussed below.

Catheter 4 includes a main body portion 16, typically about 50 to 100 cm long and a tip portion 18, typically about 5 to 25 cm long. While both main body portion 16 and tip portion 18 are flexible, tip portion 18 is preferably more flexible (less stiff) than main body portion 16. Tip portion 18 includes a main section 20 extending along most of the length of tip portion 18, and an offset, preferably reverse-angle anchor section 22. Anchor section 22, shown best in FIG. 1A, is typically about 2–6 cm long and has a pre-formed shape defining a curved section extending over an arc of about 45–180 degrees.

Tip portion 18 has a number of, typically about 10–24, band electrodes 24 along its length and a tip electrode 26 at the distal end of the anchor section 22. Electrodes 24, 26 may be constructed for both mapping and ablation.

FIGS. 2A and 2B illustrates cross-sectional views of one embodiment of the catheter shaft 28 taken along lines A—A and B—B of tip portion 18. Catheter shaft 28 defines a main lumen 30 through which a plurality of electric wires 32, one for each electrode 24, 26, extend between the electrodes and electrical connector 10. Main lumen 30 also houses a core wire 34; core wire 34 is connected to core wire control element 14 at its proximal end and to tip electrode 26 at its distal end. Alternatively, the core wire distal end can connect to an intermediate position, proximal to tip electrode 26.

Rotating control element 14 causes core wire 34 to rotate thus causing the torquing of tip portion 18. When tip portion 18 is deflected radially into a curve, rotating control element 14 causes tip portion 18 to be deflected laterally.

The type of lateral deflection, that is in-plane (where the shape of tip portion does not change) or out-of-plane (where the shape of the tip portion changes), is determined in part by where the distal end of core wire 34 is connected. That is, connecting the distal end of core wire 34 to the proximal end of tip portion 18 causes an in-plane deflection of the tip portion while connecting the distal end of core wire 34 to anchor section 22 causes the out-of-plane lateral deflection of radially deflected tip portion 18. See U.S. patent application Ser. No. 08/694,363, filed Aug. 8, 1996 now U.S. Pat. No. 5,826,576, entitled "Electrophysiology Catheter with Multi-function Wire and Method for Making" and assigned to the Assignee of the present application.

As shown in FIGS. 2A–2C, radial deflection of main section 20 of tip portion 18 is caused by pulling or pushing on a manipulator wire 36a housed within a supplemental lumen 38. Manipulator wire 36a extends from control element 12a, along catheter shaft 28 and is anchored at the junction of main section 20 and anchor section 22. In this embodiment, manipulator wire 36a is pulled to deflect tip portion 20 in the direction of arrow 40, which is the opposite direction of anchor section 22. Therefore, offset anchor section 22 is termed an offset, reverse-angle anchor section because it extends in a direction which is generally reverse of the direction of the curve placed in main section 20 of tip portion 18 by the manipulation of manipulator wire 36a. Anchor section 22 is manipulated (radially deflected) by manipulator wire 36b attached to control element 12b.

Figure 3A:
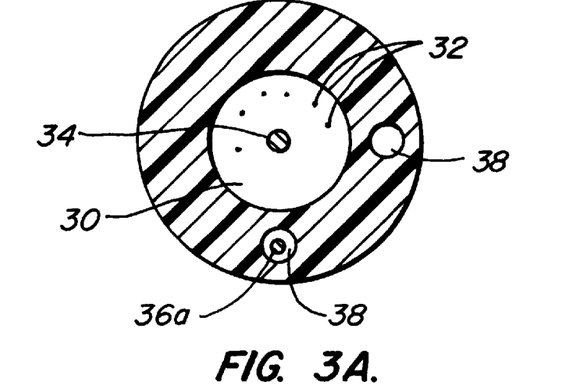
FIGS. 3A–3C are cross-sectional views taken along lines 3A—3A, 3B—3B and 3C—3C, respectively, of FIG. 2A, illustrating an alternative embodiment of the tip portion of FIG. 2A.
Figure 3B:
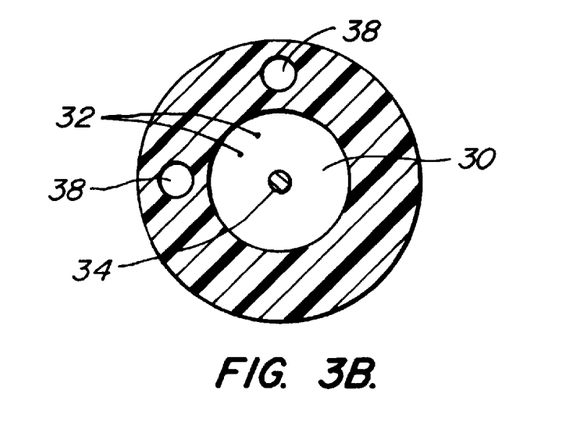
Figure 3C:
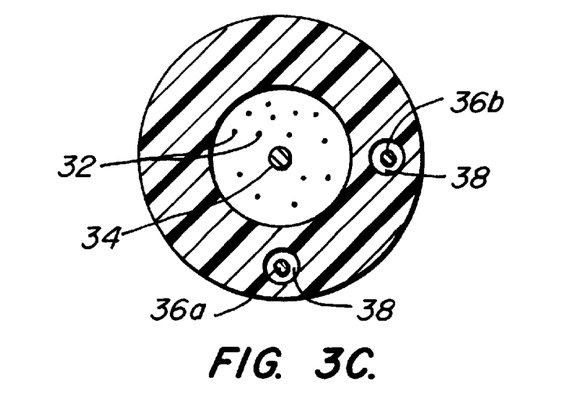

FIGS. 3A–3C illustrate another embodiment incorporating a pre-formed anchor section 22. In this embodiment, manipulator wire 36b is anchored at proximal end of tip portion 18 (see FIGS. 3C and 2A). Manipulator wire 36b is connected at its proximal end to control element 12b. Manipulator wire 36b is pulled to tilt the deflected tip section 18 sideways. Similar to the previous embodiment, manipulator wire 36a extends to the proximal end of curved anchor section 22 to radially deflect main portion 20 of tip 18 (see FIGS. 3A and 2A).

Figures 4A, 4B, 4C:
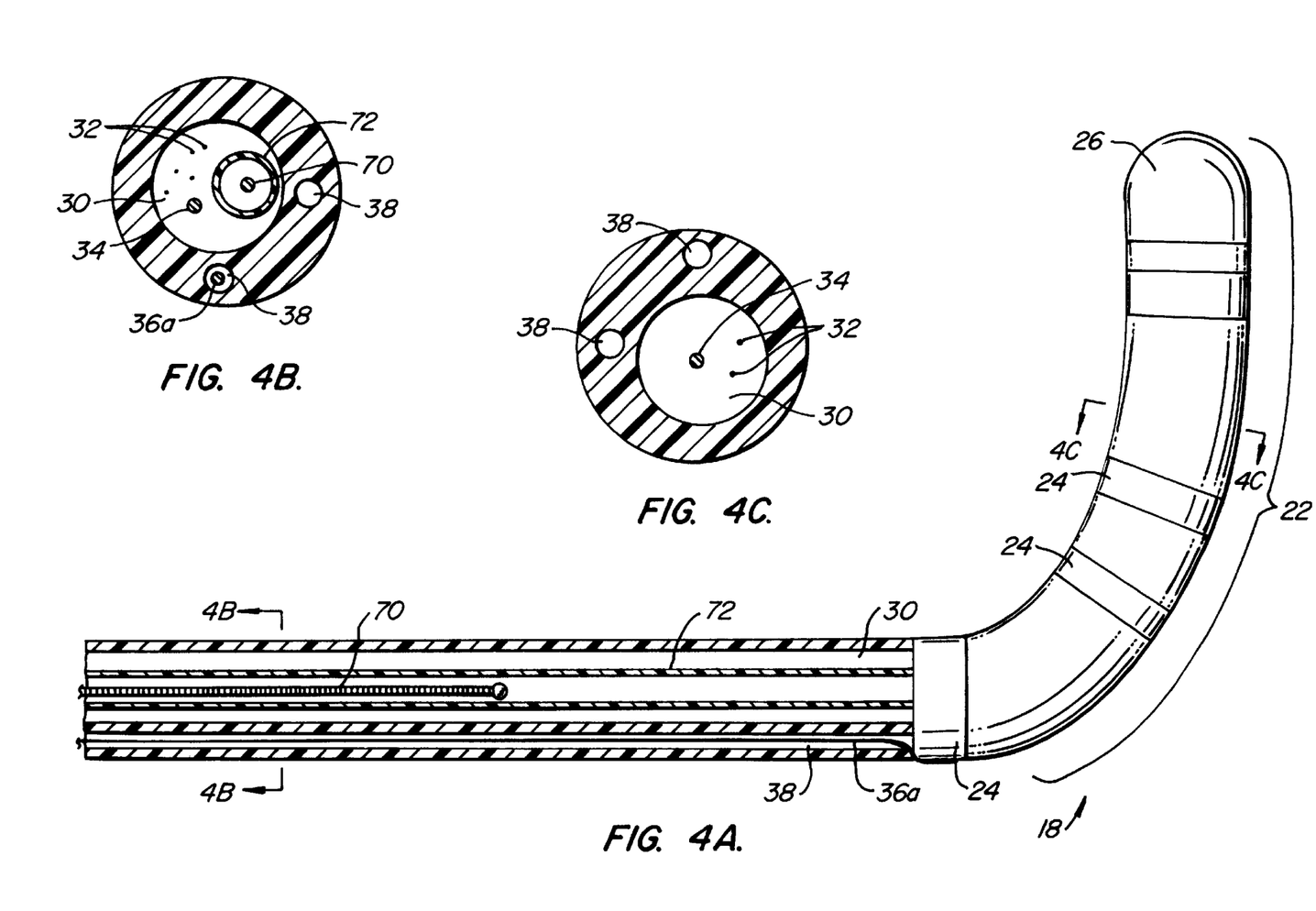
FIG. 4A is an enlarged view of another alternative tip for the catheter assembly of FIG. 1 incorporating a slidable stiffener member.
FIGS. 4B and 4C are cross-sectional views taken along lines 4B—4B and 4C—4C, respectively, of the tip of FIG. 4A.
Figure 5A:
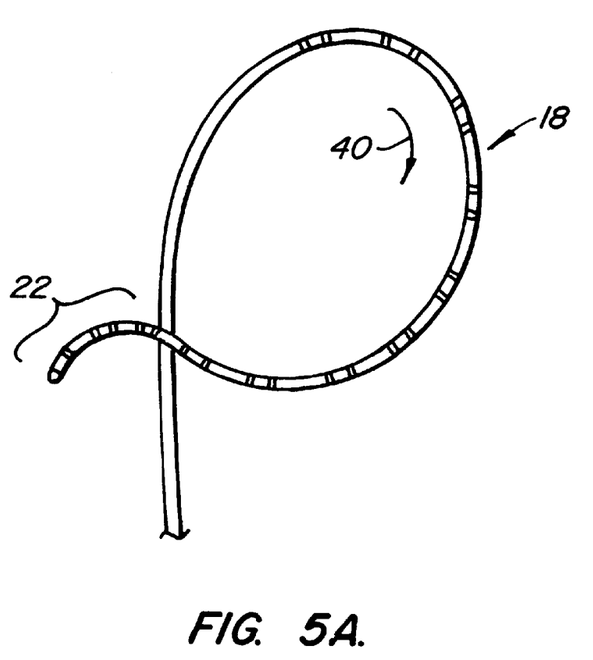
FIGS. 5A and 5B are schematic views of the tip of FIG. 4A, illustrating a method for changing the radius of the tip portion by axially sliding the stiffener member.
Figure 5B:
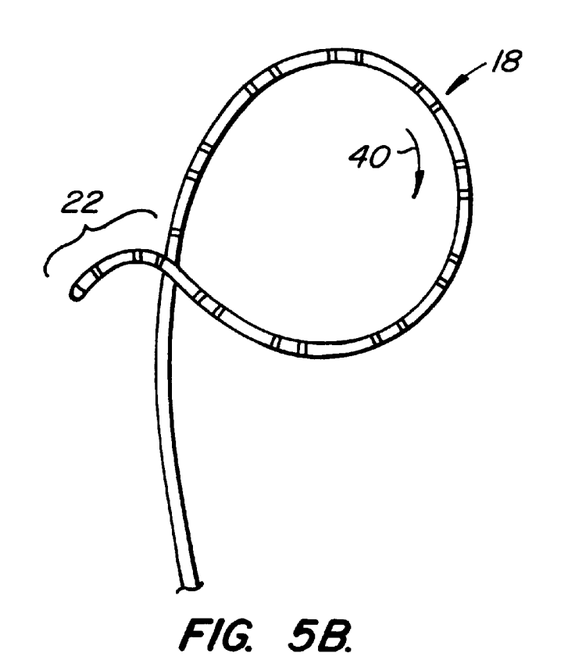

An axially slidable stiffener member 70, see FIGS. 4A–4C could be extended to different positions within tip portion 18 to change the stiffness, and thus the curvature size, of the tip portion. Stiffener member 70 extends through a protective tubing 72 within catheter tip 18. Member 70 can be actuated by a third sliding control similar to controls 12a, 12b of FIG. 1. Axially sliding stiffener member 70 in the distal direction increases the stiffness and thus the decreases the radius of tip portion 18 (see FIG. 5B), while sliding member 70 in the proximal direction decreases the stiffness and thus increases the radius of tip portion 18 (see FIG. 5A). See U.S. Pat. No. 5,487,757 entitled "Multicurved Deflectable Catheter."

Figure 6:
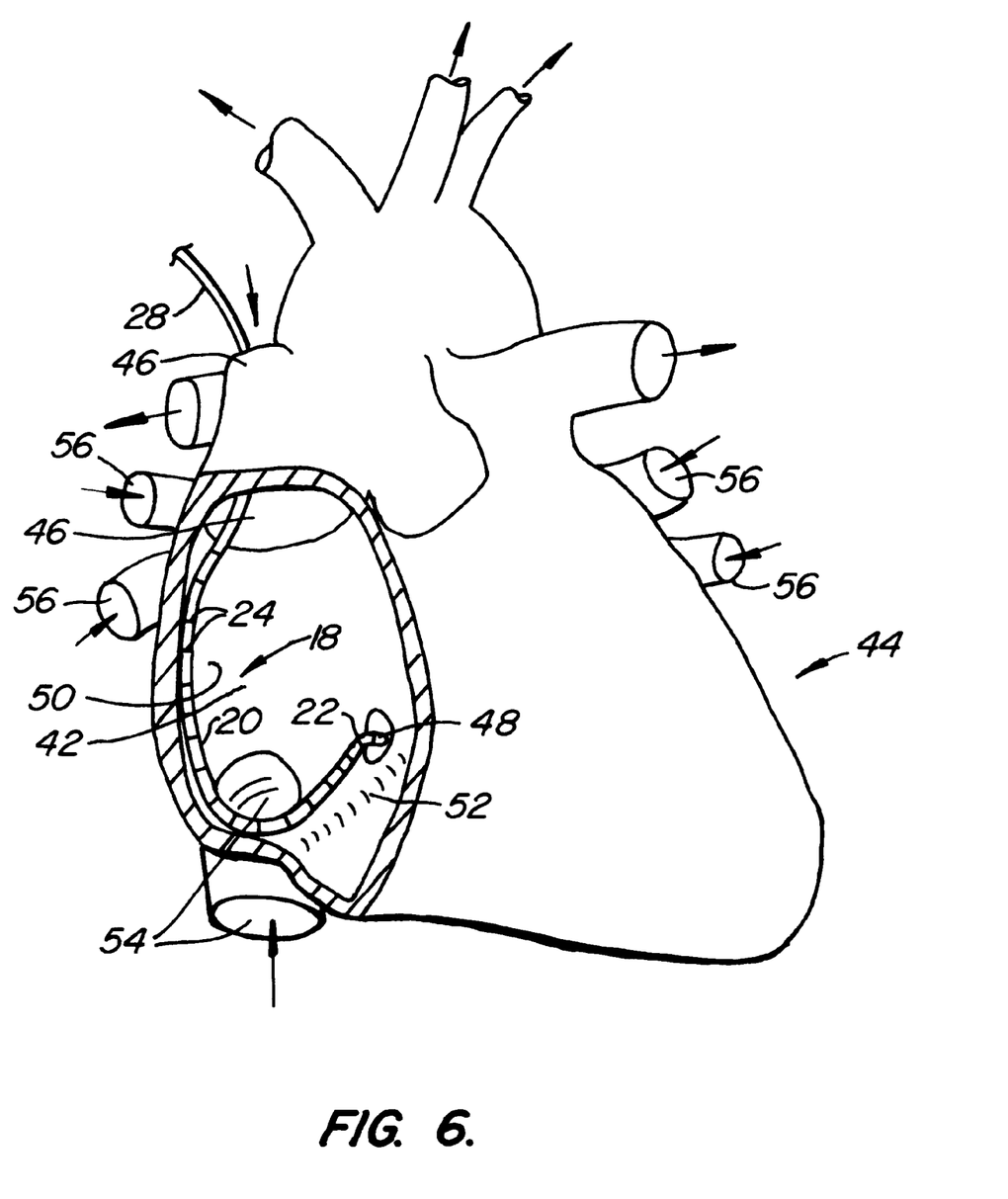
FIG. 6 shows the tip portion of the catheter of FIG. 1 introduced into the right atrium of a heart through the superior vena cava with the offset anchor section engaging the opening to the coronary sinus and the tip portion having a generally J-shape.

FIG. 6 illustrates the placement of tip portion 18 into the right atrium 42 of a heart 44. In the embodiment of FIG. 6, tip portion 18 has been introduced into right atrium 42 through superior vena cava 46 with the anchor section 22 manipulated so that it anchors at the opening 48 to the coronary sinus 49. Through the use of handle 8, manipulator wire control element 12 and core wire control element 14, tip portion 18 can be urged against the chamber wall 50; such placement is stabilized by the engagement of anchor section 22 within opening 48. FIG. 6 also illustrates the placement of section 20 of tip portion 18 against the tricus-pid annulus 52, that is the opening to the tricuspid valve. Other placements are also possible.

For atrial flutter, atrial fibrillation, and other atrial tachyardias, catheter assembly 2 provides at least the following four advantages.

1. Assembly 2 places a large number of electrodes 24, 26 in right atrium 42 to allow the physician to assess activation, that is, how conduction is propagating across the atrium over time. The electrodes can be placed in a variety of positions in the atrium, with particular emphasis on the following. In typical atrial flutter, a macro reentrant circuit usually rotates around tricuspid annulus 52, an anatomical obstacle to electrical conduction. Positioning tip portion 18 so that electrodes 24 circle the tricuspid valve allows a physician to assess conduction around the structure to look for zones of slowed conduction, which are typically targets for ablation.

Figure 15:
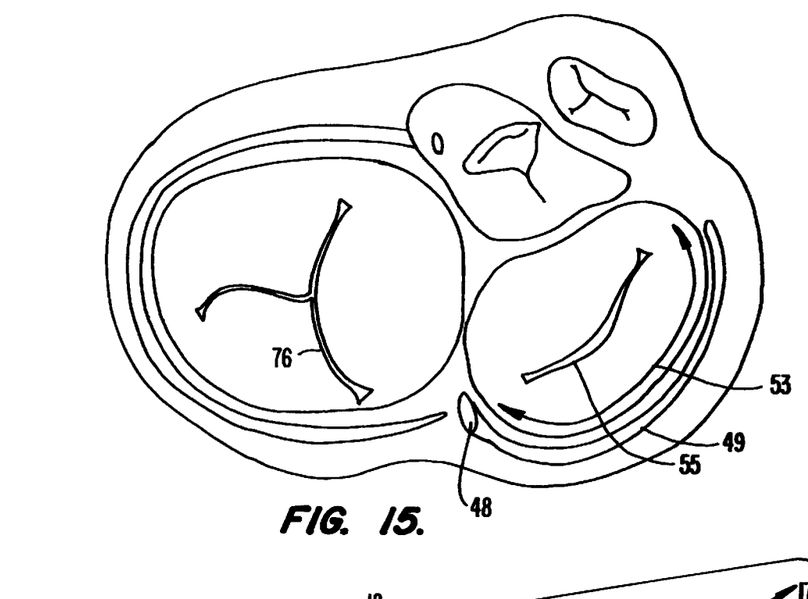
FIG. 15 is a simplified cross-sectional view of a heart illustrating the coronary sinus, tricuspid valve, mitral valve and mitral valve annulus.

2. Placing electrodes 24, 26 in the coronary sinus allows a physician to understand electrical propagation down the structure. As the coronary sinus extends from the right atrium at opening 48, it wraps around the mitral valve annulus 53 (adjacent the mitral valve 55, see FIG. 15), a left side structure, so that mapping conduction in this region can provide useful information regarding conduction between the left and right atria. With the present invention atrial mapping electrodes and coronary sinus mapping electrodes are combined on a single catheter; a better picture of electrical conduction between these structures is thus available. Also, a single catheter assembly 2 can replace two separate catheters in some cases.

3. In atrial flutter ablation situations, pacing from the coronary sinus and recording from electrodes 24 in right atrium 42 is a very useful technique for demonstrating conduction block after creating RF lesions between anatomical landmarks, such as tricuspid annulus 52 and inferior vena cava 54. This technique could also prove useful for assessing conduction block after the creation of linear lesions for atrial fibrillation.

4. As mentioned above, atrial fibrillation can involve both left and right atria. In the left atrium, evidence has shown that pulmonary veins 56 are anatomical barriers to conduction which may play an important role. Therefore, catheter assembly 2 could prove useful in mapping and pacing to assess conduction block in the left atrium. In such cases, anchor section 22 would be placed in the openings to one of the four pulmonary veins 56 (see FIGS. 9A and 9b).

Figure 7:
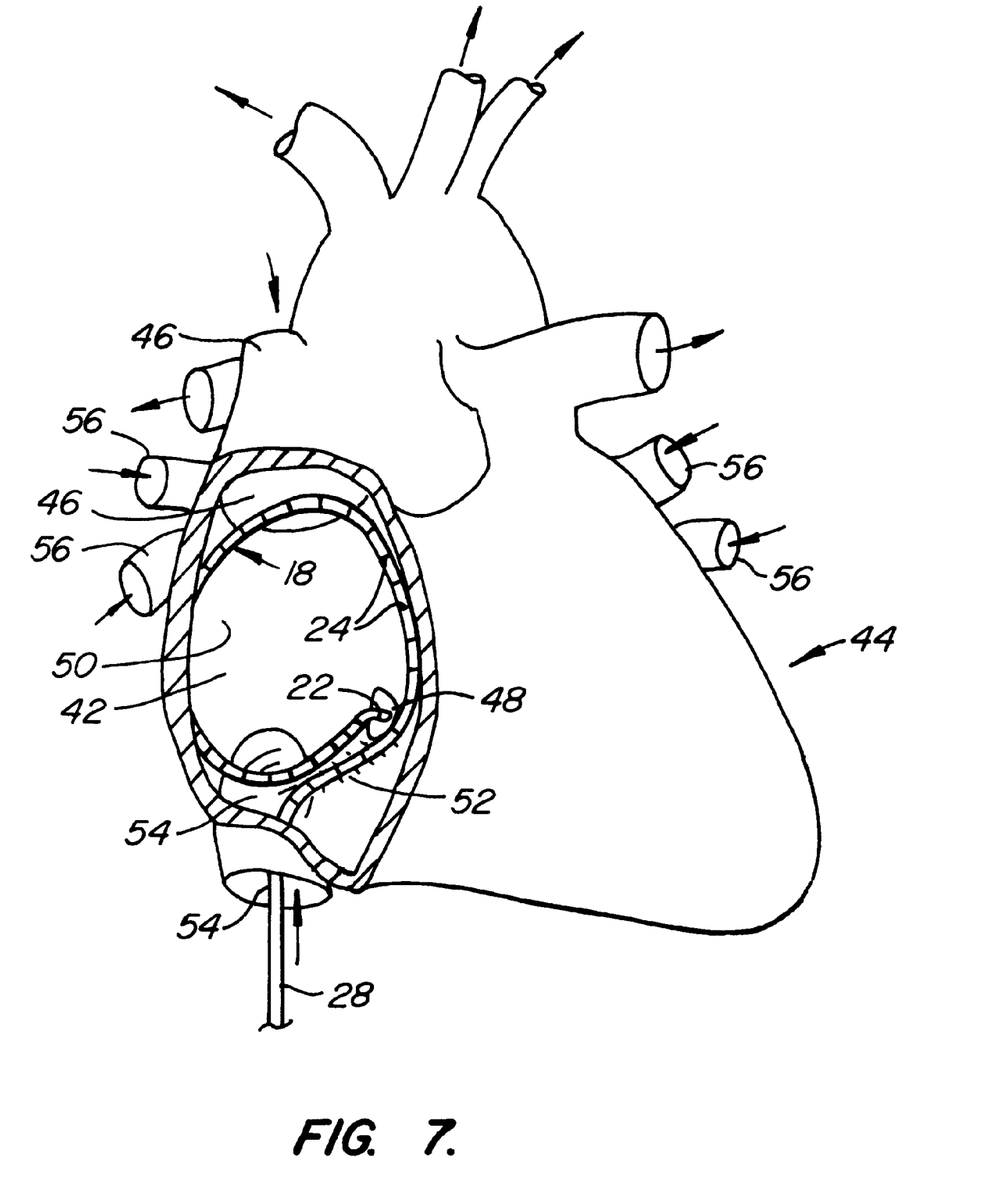
FIG. 7 illustrates introduction of the tip portion of an alternative embodiment of the catheter of FIG. 1 into the right atrium through the inferior vena cava, the tip portion curving more than 360° to form an overlapping loop with the anchor section engaging the opening to the coronary sinus.

FIG. 7 illustrates an alternative embodiment of catheter assembly 2 introduced into right atrium 42 of heart 44 through inferior vena cava 54. This embodiment is substantially the same as the embodiment of FIGS. 1 and 6 except that tip portion 18 is longer. Using this embodiment, main section 20 of tip portion 18 curves more than 360° and forms an overlapping loop, again with anchor section 22 within the opening 48 to the coronary sinus to anchor the distal end of the catheter tip portion within the heart. In either event, that is whether tip portion 18 is introduced through superior vena cava 46 of inferior vena cava 54, main section 20 of tip portion 18 is maneuvered to press against chamber wall 50.

Figure 8A:
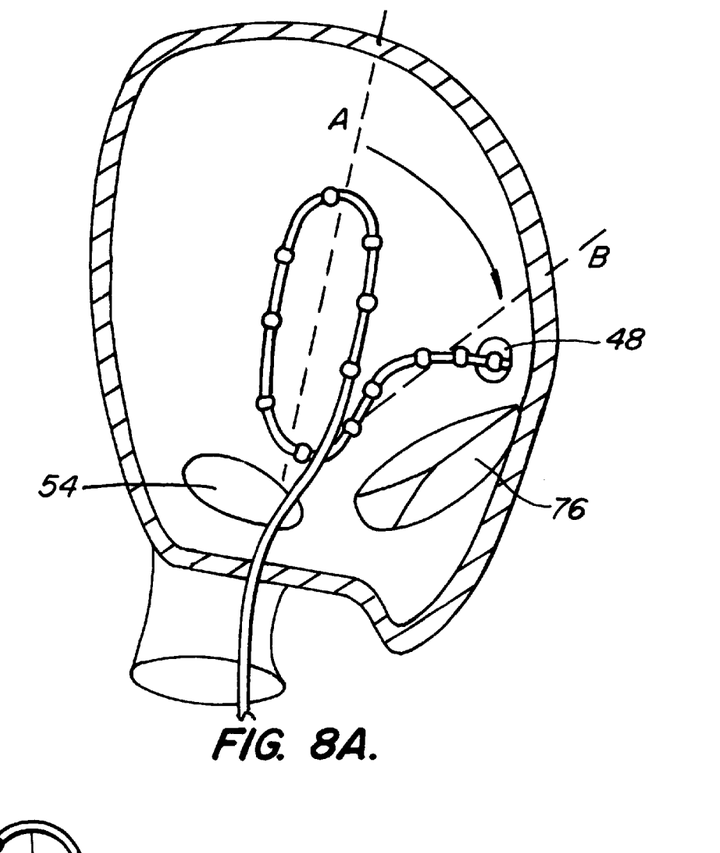
FIGS. 8A–8C illustrates a method of tilting the overlapping loop portion of the catheter tip sideways into engagement with the tricuspid valve.
Figure 8B:
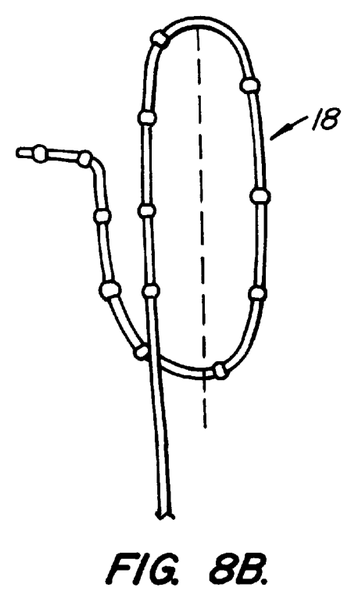
Figure 8C:
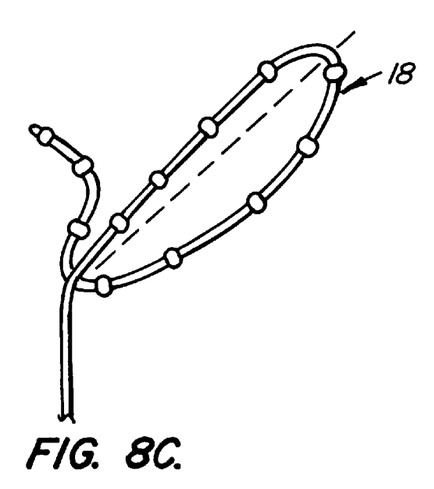

FIGS. 8A–8B illustrate a method of engaging the tricuspid valve 76 within the right atrium 42 of the heart with the overlapping loop 74 of tip portion 18. As shown, tip portion 18 is introduced into the heart chamber and overlapping loop 74 is formed therein. Manipulator wire 36b, as in the embodiment of FIGS. 3A–3C, is actuated to tilt loop 74 sideways against the tricuspid valve 76. FIG. 8A shows tip portion 18 with a primary loop but no tilt. To achieve this, distal manipulator wire 36a is activated, but not proximal manipulator wire 36b. FIG. 8D shows how the loop tilts sideways to match the angle of tricuspid valve 76 when manipulator wire 36b is activated. Alternatively, a version of the catheter which does not have proximal manipulator wire 36b can still be maneuvered against tricuspid valve annulus 52. This design is described below with reference to FIGS. 10–11. For this design, anchor section 22 is placed in coronary sinus 49, then a loop is formed by pulling manipulator wire 36, and the loop is rotated into place against tricuspid annulus 52 by torquing main body portion 16 through the rotation of handle 8.

Figure 9A:
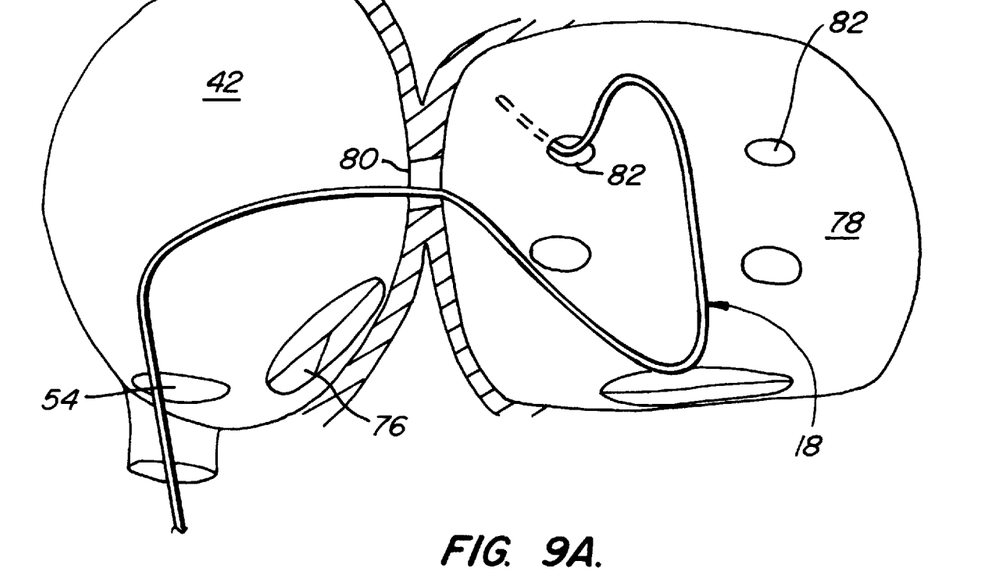
FIGS. 9A and 9B illustrate methods for introducing the catheter tip through a transseptal penetration, into the left atrium, and through a pulmonary vein ostium.
Figure 9B:
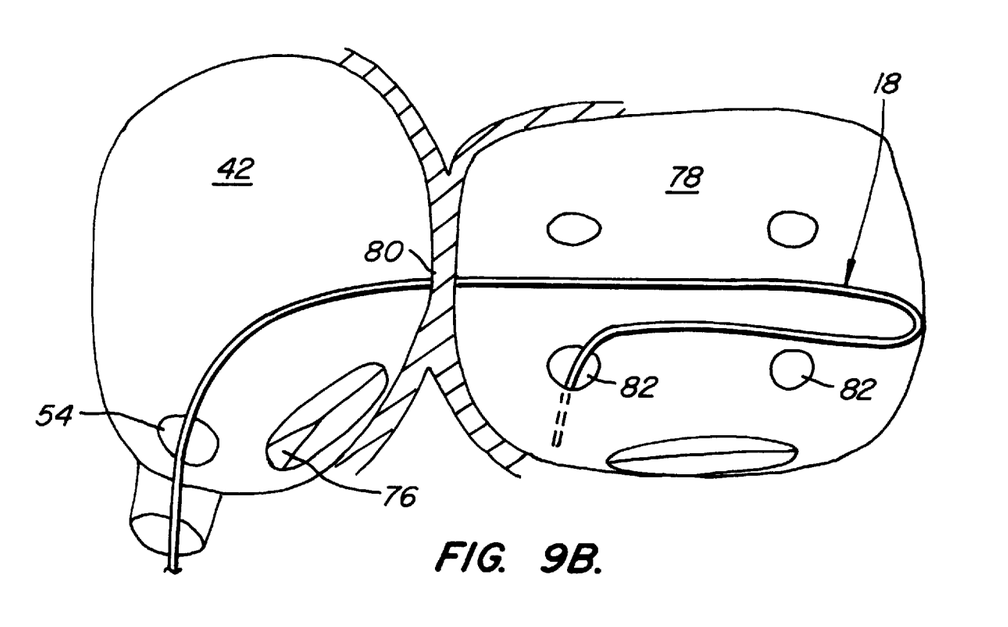

FIGS. 9A and 9B illustrate a method of delivering tip portion 18 of the catheter into left atrium 78. As shown, tip portion 18 is introduced into right atrium 42 and delivered through a transseptal puncture 80 into left atrium 78. Tip portion 18 is then manipulated to pass through one of the pulmonary vein openings 82 in left atrium 78. This manipulation may require tip portion 18 to have a substantially vertical position (FIG. 9A) within left atrium 78, a substantially horizontal position (FIG. 9B) in the left atrium or other configurations depending on the particular procedure. Manipulation of tip section 18 into various positions in left atrium 78 can be facilitated by anchoring anchor section 22 into a pulmonary vein opening 82 as shown. The resulting improved contact between the electrodes and left atrial tissue can facilitate the mapping and ablation of atrial fibrillation and other atrial tachycardias.

Figure 10:
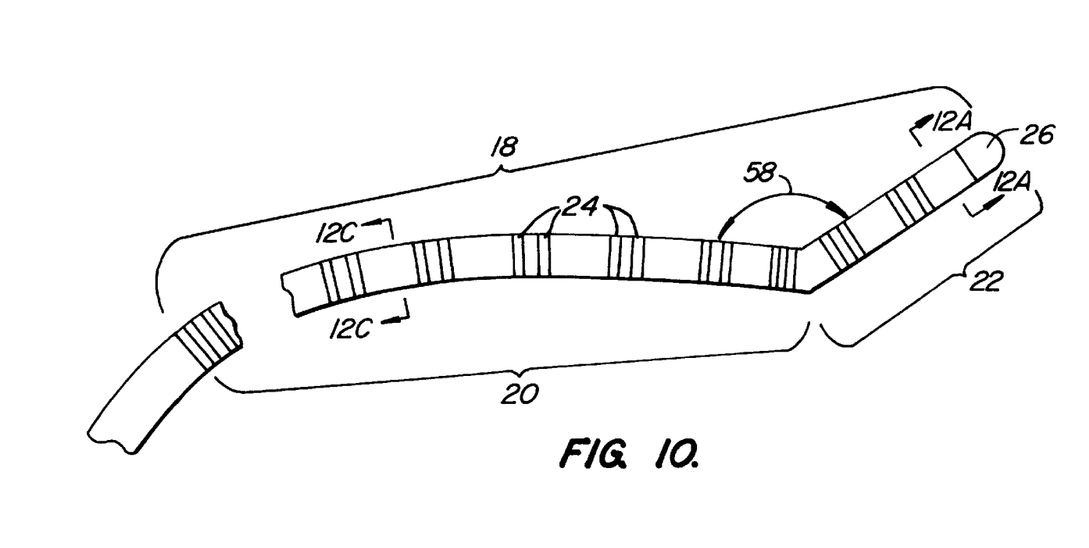
FIG. 10 is a side view of the tip portion of a preferred embodiment of the invention.

FIG. 10 illustrates the tip portion 18 of an alternative embodiment of the invention. Anchor section 22 is an essentially straight section defining an angle 58 to the distal end of main section 20. Angle 58 preferably ranges from about 45° to about 180°, and more preferably is about 140°, while the length of anchor section 22 is preferably about 1 to 6 cm long, and more preferably is about 4 cm long. With the embodiment of FIG. 10 only a single manipulator wire 36 is used.

Figure 11:
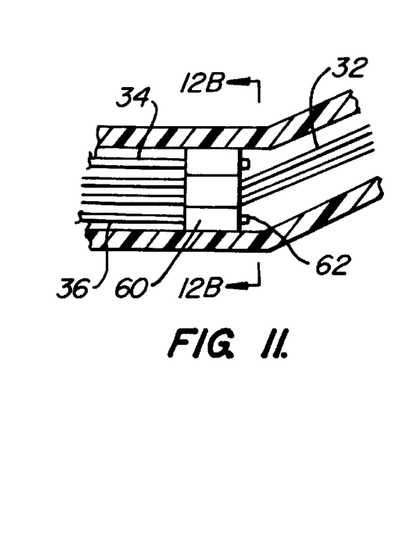
FIG. 11 is an enlarged cross-sectional view taken at the joint between the main section and anchor section of the tip portion of FIG. 10.
Figure 12A:
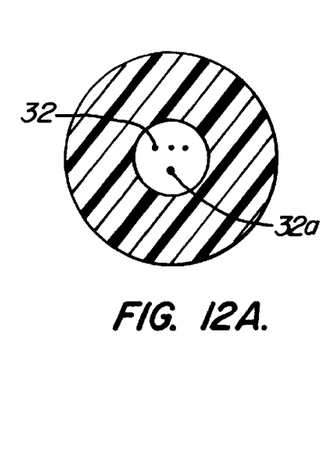
FIG. 12A is a cross-sectional view taken along line 12A—12A of FIG. 10.
Figure 12B:
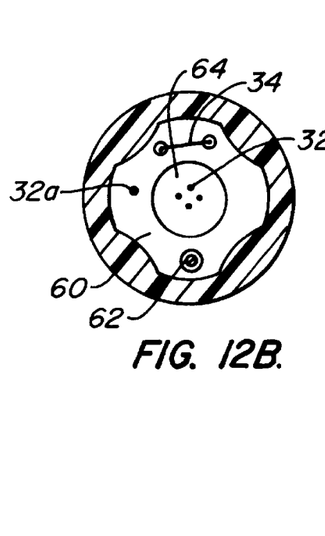
FIG. 12B is a cross-sectional view taken along line 12B—12B of FIG. 11.
Figure 12C:
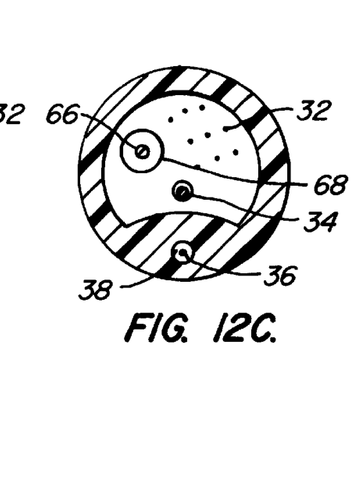
FIG. 12C is a cross-sectional view taken along line 12C—12C of FIG. 10.

The distal end of manipulator wire 36 passes through an insert 60, see FIGS. 11 and 12B, and is prevented from pulling back through the insert 60 by a ball 62 at its distal end. Core wire 34 also terminates at insert 60 by passing through the insert and then doubling back over to a second bore formed in the insert for receipt of the core wire 34. This is also illustrated in FIGS. 11 and 12B. Insert 60 has a center bore 64 through which electrical wires 32, connected to electrodes 24 along anchor section 22, pass. Tip electrode 26 has its electrical wire 32a pass through insert 60 in a manner to be embedded within and affixed to insert 60 as illustrated in FIG. 12B. This securing of wire 32a to insert 60 is a safety feature to help ensure that tip electrode 26 does not become dislodged from anchor section 22. An alternative to the separate tip electrode 26 is a thermally formed rounded plastic tip, formed from the tip tubing itself. This design is described in patent application Ser. No. 08/511,823, filed Aug. 7, 1995 and entitled "simplified Torquing Electrode Catheter."

Figure 13:
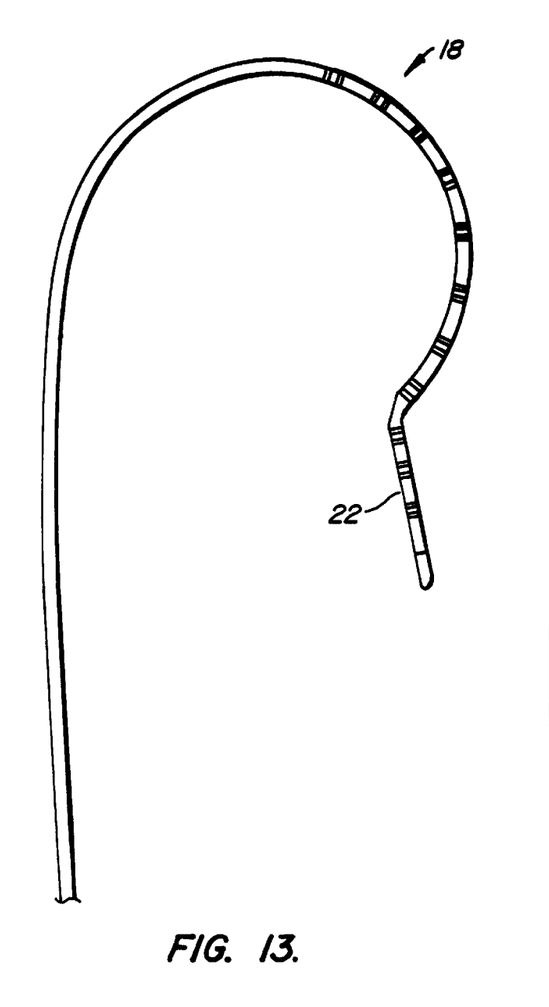
FIG. 13 illustrates the tip portion of FIG. 10 with the slide wire fully retracted so that radial deflection of the tip portion results in a larger diameter curve because the proximal section is softer due to retracted slidable stiffener member.
Figure 14:
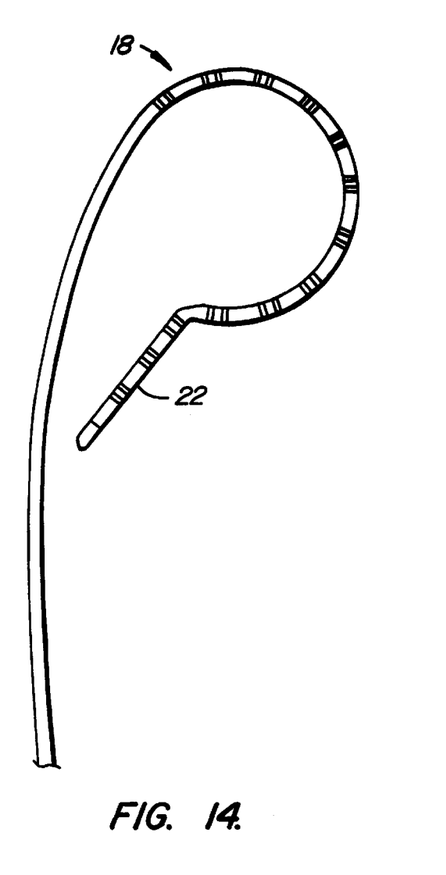
FIG. 14 illustrates the tip portion of FIG. 13 with the slide wire fully extended so that radial deflection of the tip portion creates a smaller diameter curve because the proximal tip portion is stiffer.

Instead of two manipulator wires 36, the embodiment of FIG. 10 includes one manipulator wire 36 and a slide wire 66 which connects to control element 12b at proximal end assembly 6. Slide wire control element 12b causes the distal end of slide wire 66 to move along the length of main section 20 of tip portion 18. To help prevent damage to any other components and to ensure smooth operation of the slide wire, slide wire 66 is housed within a polyimide sleeve 68. When slide wire 66 is fully extended, that is moved to its most distal position, section 20 of tip portion 18 is stiffer than when slide wire 66 is pulled to its most proximal position. FIG. 13 illustrates the shape of tip portion 18 when slide wire 66 is moved to its most proximal position and manipulator wire 36 is pulled to create a larger diameter curve. FIG. 14 illustrates the shape of tip portion 18 when slide wire 66 is advanced to its most distal position and manipulator wire 36 is pulled to create a smaller diameter curve.

Figure 16:
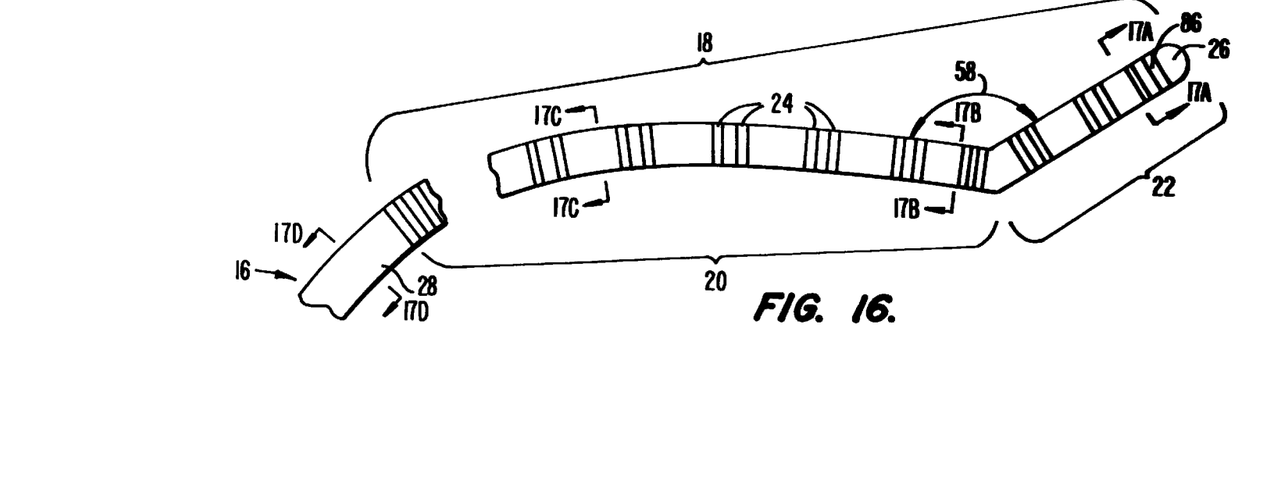
FIG. 16 is a side view similar to that of FIG. 10 of a further embodiment of the invention.
Figure 17A:
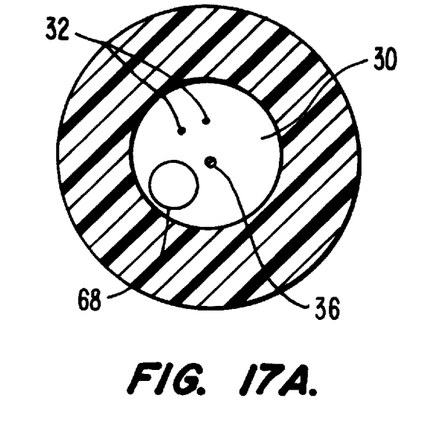
FIGS. 17A–17D are enlarged cross-sectional views of the embodiment of FIG. 16 taken along lines 17A—17A, 17B—17B, 17C—17C, and 17D—17D, respectively.
Figure 17B:
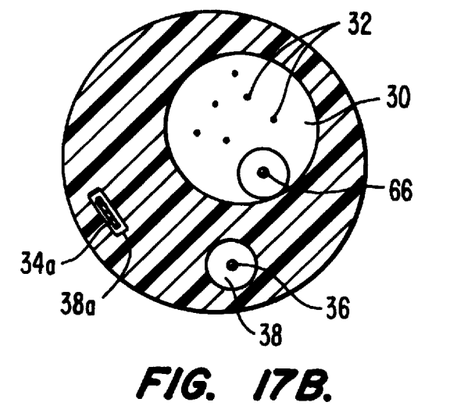
Figure 17C:
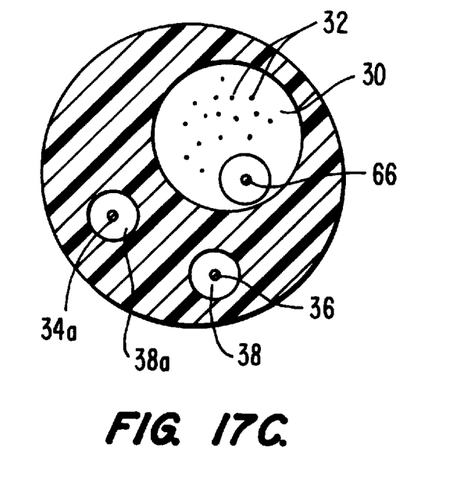

FIG. 16 illustrates tip portion 18 of a preferred embodiment of the invention which is very similar to that of FIG. 10 in function. The embodiment of FIG. 16 is preferred because it is easier to manufacture than the embodiment of FIG. 10. Anchor section 22 includes main lumen 30 (see FIG. 17A) housing sleeve 68, manipulator wire 36, and electric wires 32. Sleeve 68 is, as in the prior embodiments, used for accommodating the extension of slide wire 66. FIGS. 17B and 17C illustrate the formation of main lumen 30 as well as supplemental lumens 38, 38a along main section 20. Manipulator wire 36 is housed within supplemental lumen 38 while core wire 34 extends through supplemental lumen 38a.

Figure 17D:
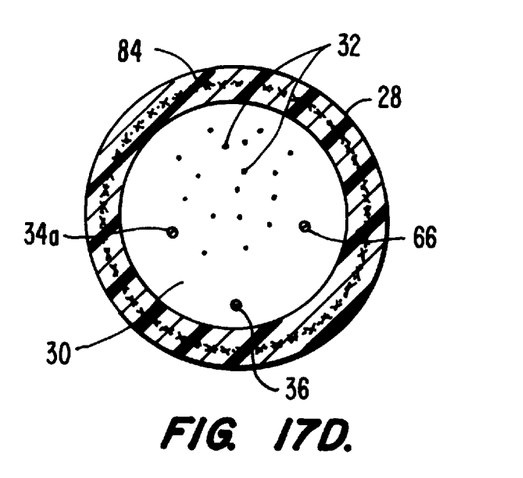

As shown in FIG. 17D, the distal end of supplemental lumen 38a has a flattened rectangular shape as does the distal end of core wire 34a. This provides a relatively simple but effective means for providing torque transmission from core wire 34a to tip portion 18; in this embodiment the torque is transmitted to the distal end of main section 20 of the tip section.

FIG. 17D illustrates the use of strengthening braid 84 as a part of catheter shaft 28 along main body portion 16. There is only the single main lumen 30 along main body portion 16 within which electric wires 32, core wire 34a, manipulator wire 36, and slide wire 66 are housed.

The primary distinction between the embodiment of FIGS. 16 and 17A–17D is that catheter shaft 28 along main section 20 defines three lumens through which the various elements pass. There is no separate insert 60 as in the embodiment of FIGS. 10–12C. Rather, core wire 34a is rotatably coupled to tip portion 18 by the shape of the distal ends of core wire 34a and supplemental lumen 38a. In addition, manipulator wire 36 does not terminate at the junction of sections 20, 22 but rather extends to an insulating anchor 86 positioned adjacent tip electrode 26. It has been found that using this construction, manipulator wire 36 can be pushed or pulled to cause corresponding radial deflection of main section 20 of tip portion 18, but without substantially affecting the shape of either anchor section 22 or angle 58 due to the central location of manipulator wire 36.

Figures 18, 19A:
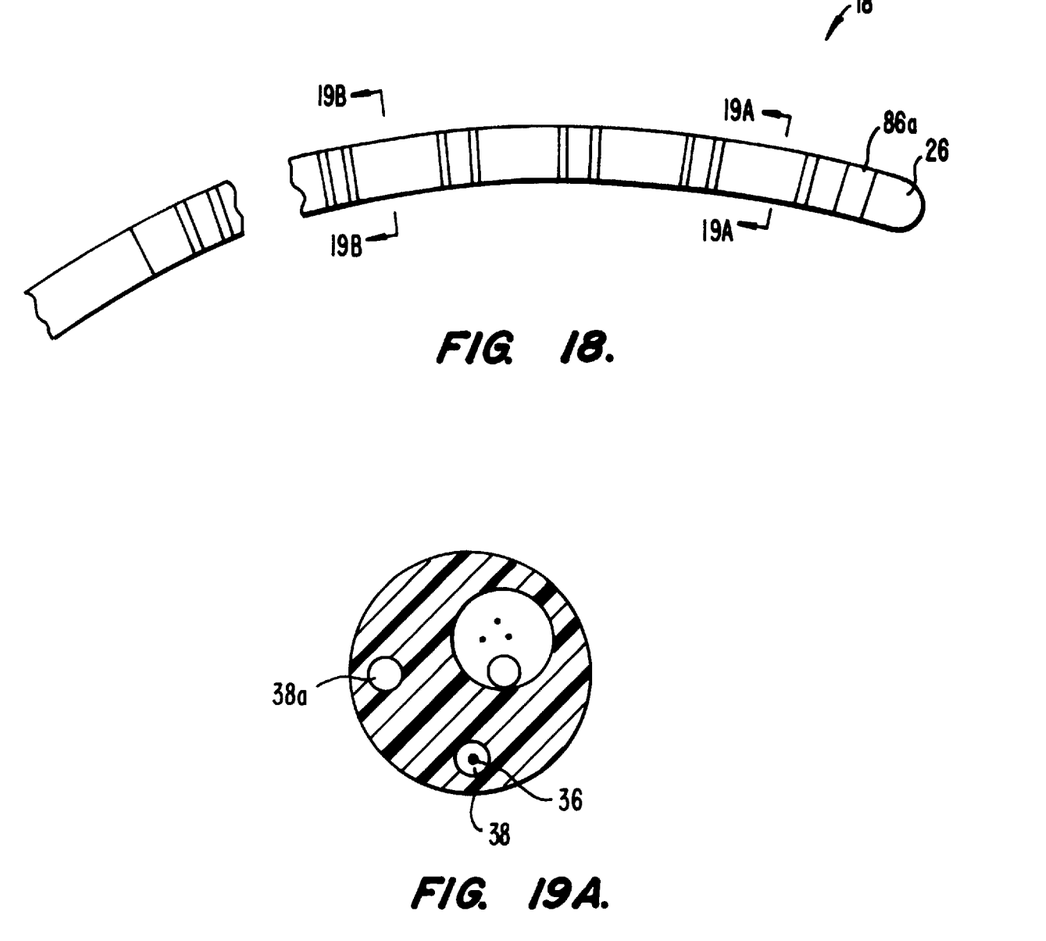
FIG. 18 is a side view of a tip portion of an embodiment of the invention lacking the offset, reverse angle anchor section of the embodiment of FIGS. 10 and 16.
FIGS. 19A and 19B are cross-sectional views of the embodiment of FIG. 18 taken along lines 19A—19A and 19B—19B, respectively.
Figure 19B:
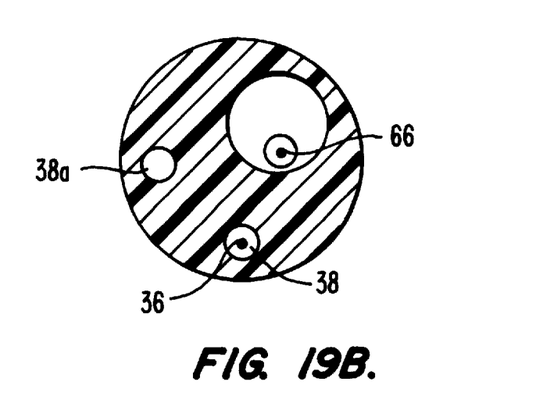

FIGS. 18, 19A and 19B show still a further embodiment of a tip 18 which omits or deletes anchor section 22. The embodiment of FIGS. 18–19B does not use a core wire 34a, which would provide lateral deflection, but does have a manipulator wire 36 for radial deflection of tip portion 18. In addition, slide wire 66 is used to permit the size of the radial deflection curve to be changed. Manipulator wire 36 is secured to and terminates at an insulating anchor 86a adjacent to electrode 26 by being doubled over similar to the way core wire 34 is secured to insert 60 as shown in FIGS. 11 and 12B. The final 1 cm of tip 18 adjacent anchor 86a has a single, centrally-positioned lumen to enhance bonding to anchor 86a and thus improve the ease of assembly of the catheter. The embodiment of FIGS. 18–19B, while lacking the ability to be anchored to opening 48 of coronary sinus 49 as in the above-described embodiments, it is somewhat simpler in construction, and thus, more economical, and is quite suited for general purpose mapping, pacing and ablation throughout the atrium.

The disclosure of each patent and patent application referred to above is incorporated by reference.

Modification and variation can be made to the disclosed embodiments without departing from the subject of the invention as defined in the following claims. For example, band electrodes 24 could be replaced by, for example, long coil electrodes, especially if they are used for ablation. The shape of offset, reverse-angle anchor section 22 could have other shapes, such as a 360° loop or spiral coil, designed to engage the opening 48 to the coronary sinus, or other cardiac openings such as the openings to pulmonary veins 56.

What is claimed is:

1. A method for positioning an electrophysiology catheter comprising the following steps:

selecting an electrophysiology catheter having a tip portion with a radially deflectable main section and a straight anchor section defining an angle in the range of 45 to 180°;

introducing the tip portion of the electrophysiology catheter into a heart chamber;

adjusting a stiffness of the tip portion after the introducing step;

inserting at least a part of the anchor section into an opening in a wall of the heart chamber; and manipulating the main section of the tip portion so at least a part of said main portion presses against the chamber wall along a desired path.

2. The method according to claim 1 wherein said selecting step is carried out by selecting an electrophysiology catheter having at least two electrodes along said main section and at least two electrodes along said anchor section.

3. The method according to claim 2 wherein said selecting step is carried out so that said electrodes comprise ablation-capable electrodes along at least one of said main section and said anchor section.

4. The method according to claim 1 wherein said introducing step comprises the step of passing the tip portion through an inferior vena cava and into a right atrium, and the inserting step is carried out using an opening to a coronary sinus as said opening in the wall of the heart chamber.

5. The method according to claim 4 wherein said introducing step includes the step of radially deflecting said tip portion more than 360°.

6. The method according to claim 1 wherein said manipulating step is carried out with said desired path extending along a tricuspid valve annulus.

7. The method according to claim 1 wherein said introducing step comprises the step of passing the tip portion through a superior vena cava and into a right atrium, and the inserting step is carried out using an opening to a coronary sinus as said opening in the wall of the heart chamber.

8. The method according to claim 7 wherein said manipulating step is carried out with said desired path extending along a tricuspid valve annulus.

9. The method according to claim 1 wherein said introducing step comprises the step of passing the tip portion through transseptal puncture and into a left atrium, and the inserting step is carried out using an opening to a pulmonary vein as said opening in the wall of the heart chamber.

10. The method according to claim 1 wherein said manipulating step comprises the steps of radially and laterally deflecting said tip portion.

11. The method according to claim 1 wherein said manipulating step comprises the step of laterally deflecting said tip portion.

12. The method according to claim 11 wherein said laterally deflecting step is carried out by torquing a core wire having a distal end connected to the tip portion.

13. The method according to claim 11 wherein said laterally deflecting step is carried out by torquing the catheter.

14. The method according to claim 1 wherein the selecting step is carried out so the anchor section is about 4 cm long and extends at an angle of about 140° to the main section.

15. The method according to claim 1 wherein the anchor section is an offset, reverse-angle anchor section.

16. A method for performing an electrophysiology procedure comprising the following steps:

selecting an electrophysiology catheter having a tip portion with a radially deflectable main section and an offset anchor section at the distal end of the tip portion;

introducing the tip portion of the electrophysiology catheter into a heart chamber;

adjusting a stiffness of the tip portion after the introducing step;

inserting at least a part of the anchor section into an opening in a wall of the heart chamber;

positioning the main section of the tip portion against the chamber wall along a desired path operating said electrodes; and operating said electrodes.

17. The method according to claim 16 wherein the operating step is carried out by using the electrodes to map said desired path.

18. The method according to claim 16 wherein the operating step is carried out using the electrodes to ablate tissue along at least one of the main section and anchor section.

19. The method according to claim 16 wherein the positioning step is carried out so at least a portion of the desired path is along a tricuspid annulus.

20. A stabilized electrophysiology catheter comprising:

a catheter shaft having a main body portion and a flexible tip portion, the tip portion terminating at a distal end;

a plurality of electrodes along said tip portion;

a manipulator element extending along the catheter shaft;

a first radial deflector element, extending along the catheter shaft, coupled to the tip portion whereby at least a part of the main section of the tip portion is radially deflectable in a first direction by longitudinal movement of the manipulator element; and the tip portion having an adjustable stiffness and comprising a main section and a distal section at said distal end of said tip portion, said distal section comprising a straight anchor section defining an angle in the range of 45 to 180° between the straight anchor section and the main section and configured to engage with an anchor to a coronary opening.

21. The catheter according to claim 20 wherein the straight anchor section is an offset, reverse-angle anchor section extending in a second direction generally opposite said first direction.

22. The catheter according to claim 20 wherein said tip portion is configurable to a generally J-shaped configuration when introduced through a superior vena cava.

23. The catheter according to claim 20 wherein said tip portion is configurable to an overlapping loop configuration when introduced through an inferior vena cava.

24. The catheter according to claim 20 wherein said anchor section is a pre-formed section.

25. The catheter according to claim 20 wherein the anchor section is about 4 cm long and the angle is about 140°.

26. The catheter according to claim 20 wherein the manipulator element is capable of deflecting the main portion at least 180°.

27. The catheter according to claim 20 wherein said catheter shaft comprises a torquable core wire non-rotatably coupled to the tip portion.

28. The catheter according to claim 20 wherein said electrodes extend along said main section and said anchor section.

29. The catheter according to claim 20 wherein said anchor section is configured to engage with and anchor to an opening to a coronary sinus.

30. The catheter according to claim 20 wherein said electrodes are mapping electrodes.

31. The catheter according to claim 20 further comprising a longitudinally-movable stiffening mandrel within the catheter shaft so said deflectable main section is an adjustable-radius, deflectable main section.

32. The catheter according to claim 20 further comprising a second radial deflector element, whereby actuating the second radial deflector element when the main section is in a curved configuration causes the curved main section to deflect laterally.

33. The catheter according to claim 32 wherein the deflectable main section is movable into an overlapping loop configuration, wherein actuating the second radial deflector element causes the looped main section to be deflected laterally to position the electrodes at an angle approximating that of the tricuspid valve annulus of the right atrium.

34. The catheter according to claim 20 wherein the tip portion is movable to an overlapping loop configuration so that torquing the main body portion of the catheter shaft causes the looped tip portion to be positioned at an angle approximating that of a tricuspid annulus.

35. A method for performing an electrophysiology procedure with a single electrophysiology catheter comprising the following steps:

selecting an electrophysiology catheter having a tip portion with a radially deflectable main section and a straight anchor section defining an angle in the range of 45 to 180°, said tip portion having electrodes thereal­ong;

introducing the tip portion of the electrophysiology catheter into a main heart chamber;

adjusting a stiffness of the tip portion after the introducing step;

engaging the anchor section to an opening with the heart chamber;

manipulating the tip portion so at least a part of the main section presses against the chamber wall along a desired path; and using the electrodes to perform a desired electrophysiology procedure.

36. The method of claim 35 wherein the method is carried out with the main heart chamber being the right atrium and the opening being a coronary sinus.

37. The method of claim 35 wherein the method is carried out with the main heart chamber being the left atrium and the opening being an opening to a pulmonary vein.

38. The method of claim 35 wherein the manipulating step is carried out so the tip portion assumes an overlapping loop configuration.

39. The method of claim 38 wherein the manipulating step comprises the step of torquing a proximal end of the catheter to cause the looped tip portion to be positioned against a tricuspid valve annulus.

40. The method of claim 38 wherein the manipulating step comprises the step of deflecting a second radially deflectable section to cause the looped tip portion to be positioned against a tricuspid valve annulus.

* * * * *